United States Patent [19]

Barnaby

[11] Patent Number: 4,537,063

[45] Date of Patent: Aug. 27, 1985

[54] NONSTEADY-STATE CORE HOLDER

[75] Inventor: Harold T. Barnaby, Duncanville, Tex.

[73] Assignee: Core Laboratories, Inc., Dallas, Tex.

[21] Appl. No.: 611,101

[22] Filed: May 17, 1984

[51] Int. Cl.[3] ............................................. G01N 15/08
[52] U.S. Cl. ................................................. 73/38
[58] Field of Search ........................................... 73/38

[56] References Cited

U.S. PATENT DOCUMENTS

| 2,633,015 | 3/1953 | Morris . | |
|---|---|---|---|
| 2,705,418 | 4/1955 | Reichertz et al. | 73/38 |
| 2,737,804 | 3/1956 | Herzog et al. | 73/38 |
| 2,821,680 | 1/1958 | Slusser et al. . | |
| 2,842,958 | 7/1958 | Sayre, Jr. et al. . | |
| 2,867,116 | 1/1959 | Aronfsky et al. . | |
| 3,139,747 | 7/1961 | Ferrell et al. . | |
| 3,173,500 | 3/1965 | Stuart et al. . | |
| 3,329,006 | 7/1967 | Silkin . | |
| 3,371,520 | 3/1968 | Slone et al. . | |
| 3,405,772 | 10/1968 | Wisenbaker et al. . | |
| 3,839,899 | 10/1974 | McMillen | 73/38 |
| 3,874,451 | 4/1975 | Jones et al. . | |
| 3,929,011 | 12/1975 | Jones . | |
| 4,198,853 | 4/1980 | Graham et al. . | |
| 4,253,327 | 3/1981 | Wiley . | |

FOREIGN PATENT DOCUMENTS

| 1511616 | 12/1967 | France | 73/38 |
|---|---|---|---|
| 1192033 | 5/1970 | United Kingdom . | |
| 1257835 | 12/1971 | United Kingdom . | |
| 1313093 | 4/1973 | United Kingdom . | |
| 1349738 | 4/1974 | United Kingdom . | |
| 2099157 | 12/1982 | United Kingdom . | |
| 153457 | 6/1963 | U.S.S.R. | 73/38 |

OTHER PUBLICATIONS

Jones, A Rapid Accurate Unsteady-State Klinkenberg Permeameter, Soc. Pit. Eng. J., Oct. 1972, pp. 383-397.
Walls et al., Effects of Pressure and Partial Water Saturation on Gas Permeability in Tight Sands, Soc. Pet. Eng. Paper, Sep. 1980, SPE 9378.
Freeman et al., Low Permeability Laboratory Measurements by Nonsteady State and Conventional Methods, Soc. Pet. Eng. Paper, Oct. 1981, SPE 10075.

Primary Examiner—Stewart J. Levy
Assistant Examiner—Joseph W. Roskos
Attorney, Agent, or Firm—Lee C. Robinson, Jr.

[57] ABSTRACT

A core holder is used in the nonsteady-state testing of permeability and other flow characteristics of a geological core sample. A reference pressure reservoir assembly contains a predetermined volume of test gas at a known pressure, and a gas operated valve admits this test gas rapidly to the upstream end of the core sample. The downstream end of the core sample is open to the atmosphere, and the pressure in the reference pressure reservoir assembly is monitored as it decays in time while the test gas passes through the core sample. The gas-operated valve is formed of an upstream plug, a gland fitting the plug, and a valve stem fitting into a generally cylindrical cavity formed in the plug and gland. The valve stem has an enlarged head at one end with an annular slot on a cylindrical surface thereof. This structure minimizes turbulence in the flow of the test gas through the valve assembly.

9 Claims, 4 Drawing Figures

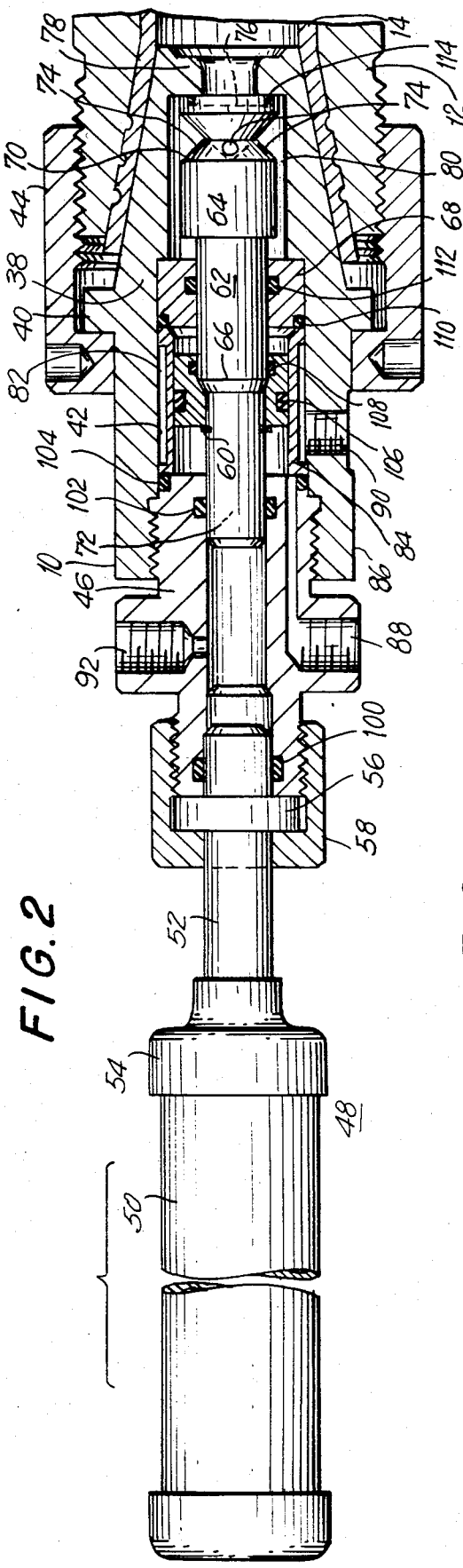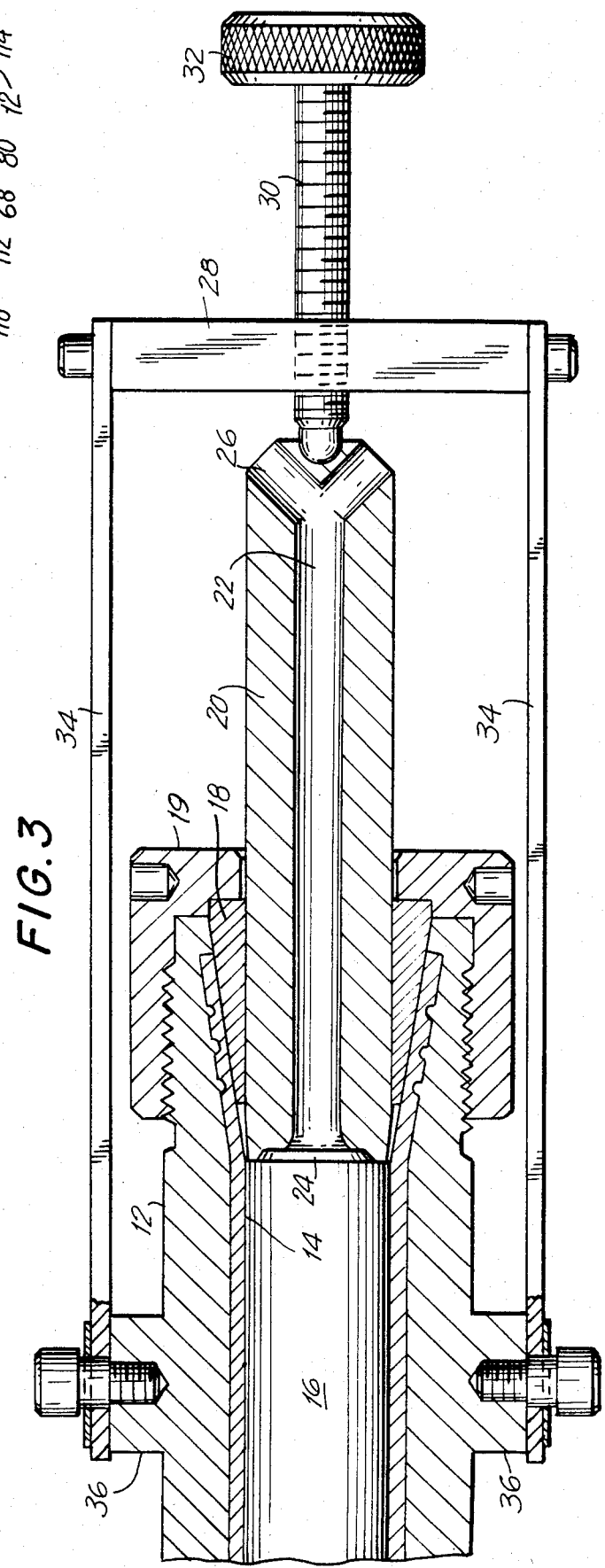

NONSTEADY-STATE CORE HOLDER

This invention relates to the measurement of flow characteristics of a rock formation, and is more specifically directed to apparatus for measuring the permeability or other flow characteristics of a rock core sample. More specifically, the invention is directed to core holder apparatus in which the flow characteristics, such as permeability of the core sample, are measured under nonsteady-state flow conditions.

Knowledge of the permeability of a sample of a rock formation taken from beneath the earth's surface is important for evaluation of the potential of petroleum deposits, natural gas formations, and the like that might be present. Permeability relates the volumetric flow rate of petroleum or natural gas to a given pressure differential through the rock formation, and is generally measured in "Darcies", "millidarcies", or "microdarcies".

Typically, permeability measuring techniques rely on the so-called "steady-state" method wherein a fluid, such as air, flows through the core sample at steady-state conditions. However, steady-state techniques can be time consuming and inefficient.

A knowledge of the permeability of the rock formation is particularly useful in oil and gas exploration, in drilling wells into rock formations, and in treating underground rock formations to improve the production of oil or gas contained therein. In the case of treating the rock formations to improved production, it is particularly important to avoid adverse affects from the treatment itself, such as corrosion, as the injection of a substance with an adverse effect on the permeability of the rock formation can have a disastrous effect on production. To this end, it is absolutely essential to have an accurate understanding of the flow characteristics of the rock formation.

To carry out testing of the permeability or other flow characteristics of a given rock formation, the core sample is removed from the rock, and is cleaned and prepared for testing. The gaseous test medium, such as compressed air, is fed to an upstream end of the core in the core holder, and the rate of flow and differential pressure between the upstream and downstream ends of the core sample is measured.

Generally, the measurement of permeability of a rock formation is taken by placing the generally cylindrical core sample in a core holder, and subjecting the core sample to a pressure corresponding to the overburden pressure at the depth of the formation represented by the core. Preferably, this pressure is applied to a sleeve around the cylindrical outer surface of the core sample. This is done because the pore size may change and microscopic cracks may result when the core sample is removed from the rock formation, and these changes will generally affect the permeability of the core sample.

The pressure differential across the core sample, if the flow rate is known, coupled with the viscosity of the gaseous test medium, allows the core sample permeability to be calculated. Other flow characteristics can also be determined.

In order to reduce the time and effort required to test geological core samples, and also to permit use of test gasses other than compressed air, the so-called nonsteady state technique has been developed. This technique is the subject of U.S. patent application Ser. No. 426,798, filed Sept. 29, 1982, and having a common assignee herewith.

This patent application Ser. No. 426,798 addresses many of the problems found in the steady-state core testing technique, such as the requirement of a great deal of time to complete.

In the nonsteady-state core testing, the difference in pressure between the upstream and downstream ends of the core sample is measured as the flow rate of the gaseous test medium changes over time. While the mathematical technique for measuring the nonsteady-state permeability is rather complex, the same can be easily handled by a small computer or microprocessor, such as a personal computer, so that the entire process of testing the core sample and calculating the permeability thereof can be completed within several minutes for each core sample.

In a non-steady state core permeability test, a known volume of the gaseous test medium, at a known initial pressure, is exhausted through the core sample, and the pressure differential between the upstream and downstream ends of the core sample is measured over time. The pressure and time data are processed in the computer, and the core permeability is calculated.

This technique appears, at first glance, to be simple and straightforward, but errors can arise if the pressurized volume of test gas is not presented immediately to the upstream end of the core sample at the beginning of the test. Other errors can occur if there are any significant obstructions, during the test, to the flow of the gaseous test medium, other than the core sample itself. For this reason, the sample holder must be provided with a valve system which can be quickly and reliably snapped into an open condition, so that the pressurized test medium will flow, substantially instantaneously, into substantially the entire upstream end of the core sample at the beginning of a test. Of course, the valve must not leak the test medium into the core sample prior to the beginning of the test.

Accordingly, it is an object of this invention to provide a core holder which is suitable for use in a non-steady-state core permeability test, and which avoids the problems inherent in previous core holders.

It is another object of this invention to provide a non-steady state core holder in which a nonsteady-state permeability test can be carried out conveniently and accurately.

It is yet another object of this invention to provide such a core holder in which a known quantity of a gaseous test medium can be presented quickly and reliably at the commencement of a core permeability test to the upstream end of the core sample, and, in which, a minimum resistance to the flow of the gaseous test medium is presented everywhere, except in the core itself.

In accordance with an aspect of this invention, a core holder apparatus is provided for carrying out non-steady-state permeability measurement of a geological core sample. In this core holder apparatus, the barrel has a core chamber therein open at its ends for holding the core sample for passage of a gaseous test medium through it. The test medium thus passes from an upstream end of the barrel, through the core sample, and out the downstream thereof. Retaining means, such as a soft rubber sleeve, within the barrel retain the core sample in the core chamber. A reference pressure reservoir contains a known volume of a gaseous test medium (i.e., compressed air), under a predetermined pressure (i.e., 200 psig). This volume, during the test, is permitted to pass from the reservoir to the upstream end of the core sample, and thence through the core sample and out the downstream end to a lower pressure drain (i.e., the open atmosphere). A gas-operated valve couples the reservoir to the upstream end of the core chamber and this valve is constructed to open rapidly for the rapid exposure of the upstream end of the core sample to the gaseous test medium when a control gas pressure is applied to an opening actuator port of the valve. A pressure monitoring device, preferably of low mass, is coupled to the reference pressure reservoir for measuring the pressure therein as it decays over time during the test. Preferably, the valve includes a hollow valve stem having a head at one end thereof, a gland overfitting an end of the valve stem and permitting slidable movement therein, a valve seat disposed about the upstream end of the core chamber sealably seating against the head when the valve stem is urged in one direction and to open when the valve stem is urged in the opposite direction. A piston element is coupled to the valve stem within a cylinder sleeve. A seating actuator port and unseating actuator port are coupled by gas conduits to upstream and downstream sides of the piston member to urge the piston member, and the associated valve stem to its closed and open positions, respectively, when the control gas is applied to the respective actuator port.

The above, and many other objects, features, and advantages of this invention will be more completely understood by consideration of the ensuing detailed description, which is to be considered in connection with the accompanying drawings, in which:

FIG. 2 is a partial cross section of the upstream end of the core holder of FIG. 1 with the valve thereof in its closed position;

FIG. 3 is a cross sectional view of the downstream end of the core holder of FIG. 1.

Figure 1:
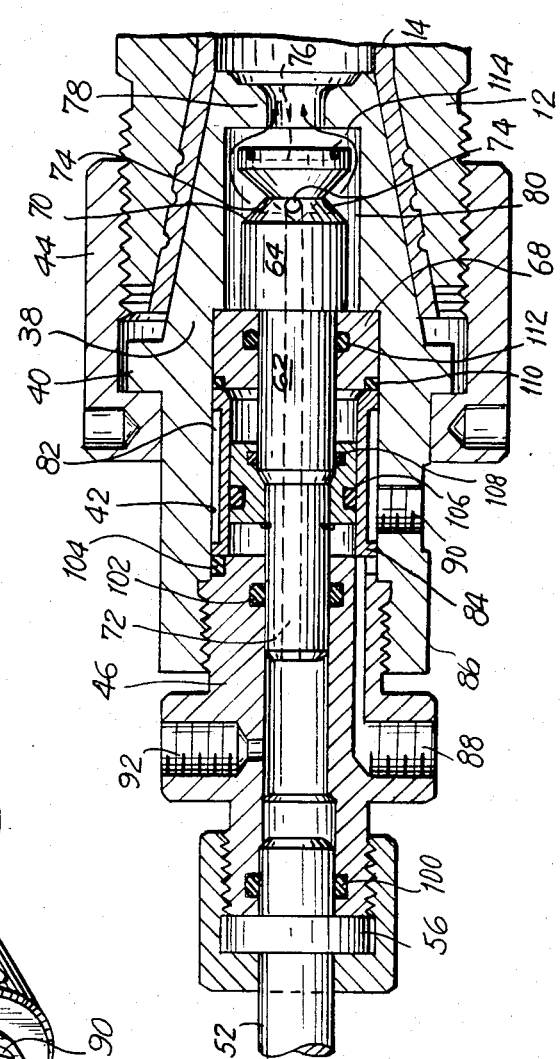
FIG. 1 is a perspective view of a core holder according to one embodiment of this invention.

With reference to FIGS. 1, 2, and 3 of the drawings, a core holder 10 according to one embodiment of this invention for use in the non-steady stage analysis of a core sample. This core holder 10 is designed to avoid large pressure drops within the system, except the pressure drop across the core sample itself. This core holder 10 is provided with a pressure-operated trigger, which opens a valve mechanism substantially instantaneously at the commencement of a permeability measurement. The design of this core holder 10 also features extremely low flow restrictions in the path of the gaseous test fluid, both on the upstream and downstream sides of the core being tested. As a result of this construction, the core holder permits testing with an extremely low error due to pressure drops within the core holder itself; this error is as low as 2.4 percent.

The core holder of this embodiment includes a barrel 12 having a cavity with flared ends and with a generally cylindrical central portion. A sleeve 14 of soft resilient material, such as rubber, is disposed within the barrel cavity, and a core chamber 16 is formed within the central, cylindrical portion of the barrel cavity within the sleeve 14. The barrel 12 and sleeve 14 are dimensioned for one particular size of core sample, and a core sample of appropriate dimensions (i.e., ¾ inch diameter by six inches in length) is disposed for testing within the core chamber 16.

With reference to FIG. 3, a downstream ferrule 18 has a conic face which fits into the flared downstream end of the core holder barrel 12. A cap 19 screws onto the barrel 12 at its downstream end to hold the ferrule 18 in place. An elongated downstream end piece 20 fits in the downstream ferrule 18, and has an exhaust air channel 22 bored therein. This channel 22 has a flared foot 24 at the downstream end of the core and a wye 26 at the downstream end of the end piece 20. This construction allows maximal unobstructed gas flow from the entire downstream end surface of the core sample, through the end piece, to the open atmosphere.

An end support plate 28 carries a support screw 30 for holding the core sample and the downstream plug 20 in place on the downstream end of the barrel 12. A knob 32 provided on the outer end of the screw 30 permits manual tightening and loosening of the screw 30. The support plate 28 is held by side plates 34 pivotally mounted on a support bracket 36 which is integral with the barrel 12.

On the upstream side of the barrel 12 there is disposed an upstream plug 38 having a generally conic face for fitting snugly into the sleeve 14 in the flared upstream portion of the barrel 12. An annular flange 40 is formed on the plug 38 approximately adjacent the conic face thereof, and a generally cylindrical bore 42 is formed within the plug 38.

A threaded cap 44 fits over the flange 40 onto a threaded portion of the upstream end of the barrel 12, and firmly secures the plug 38 to the barrel 12.

A gland 46, provided with a longitudinal bore, has male threads at either end, one of which fits into the cylindrical bore at the upstream end of the upstream plug 38.

A pressure reference chamber assembly 48 stores a predetermined volume of the gaseous test medium at a predetermined pressure, and is positioned for controllable release to the upstream core sample face. The assembly 48 is formed of a cylinder 50 coupled to a male fitting 52 by a nipple 54. The male fitting 52 fits into the upstream end of the bore in the gland 46. The male fitting 52 is provided with a flange 56, and a cap 58 fits over the flange 56 and screws onto the gland 46 to secure the reference chamber assembly 48 in place.

At the heart of the valve assembly of this embodiment is a valve stem 62, formed generally as a hollow, stepped cylinder having an enlarged head 64 formed at the downstream end thereof. A stepped section 66 in the shaft of the valve stem 62 joins a smaller-diameter upstream portion to a larger-diameter downstream portion of the valve stem 62.

An inboard bearing member 68, which is generally cylindrical, fits into the cylindrical bore 42 and divides the same into a downstream portion surrounding the head 64 in an upstream portion forming an actuator cylinder. The bearing member 68 has an axial bore, and the valve stem 62 fits slidably into it.

An annular notch 70 is provided in the head 64, and a longitudinal bore 72 in the valve stem 62 extends from an open upstream end of the stem 62 into the head 74. This bore 72 connects with a plurality of apertures 74 in the sloping upstream side of the notch 70.

This notch is favorably provided with a forty-five degree slope, at least on the downstream side thereof. In this embodiment, a forty-five degree slope is provided on the upstream side of the notch 70 as well. This construction minimizes the turbulence in the gas flow through the head 64 and facilitates unobstructed gas flow through the valve assembly.

A sealing face 76 is provided on the very upstream end of the head 64 and fits against a seat 78 in the plug 38 at the upstream end thereof. This seat 78 is located in close proximity to the upstream end of the core sample in the core chamber 16.

The cylindrical bore 72 of the valve stem 62 forms a gas release path into a chamber 80 surrounding the valve stem head 64.

The portion of the cylindrical bore 42 between the bearing 68 and the gland 46 forms a piston chamber 82 containing the mechanism for seating and unseating the sealing face 76 of the valve stem head 64 with respect to the valve seat 78. Within the piston chamber 82, a cylindrical sleeve 84 closely fits upon a piston 86 which is fitted over the stepped portion 66 of the valve stem 62. The piston 86 is rigidly held in place on the valve stem 62 by the stepped portion 66 and a retainer ring 60 recessed in a groove formed in the stem 62 at the upstream face of piston 86.

An actuator port 88 within the gland 46 connects via an attached duct to the upstream end of the piston chamber 82; another actuator port 90 in the plug 38 connects with an annular space to the outside of the sleeve 84, and a duct (not shown) is provided in the sleeve 84 at the downstream end of the piston chamber 82.

A fill port 92 connects directly with to bore in the gland 46 and a gauge port 94 (shown only in FIG. 1) is also provided in communication with the bore of the gland 46. A small silicon-chip pressure gauge PG is fitted into this port 94. This gauge, or an equivalent gauge of small mass and low resonance frequency, is preferred, because such a gauge will provide a substantially instantaneous response to rapid changes in pressure.

Also shown in FIG. 2 are a plurality of 0-ring seals. These include a seal 100 disposed between the male fitting 52 and the gland 46; another seal 102 between the gland 46 and the valve stem 62; a seal 104 between the gland 46 and the upstream plug 38; a seal 106 between the piston 86 and the sleeve 84; a seal 108 between the piston 86 and the valve steam 62; a seal 110 between the inboard bearing 68 and the sleeve 84; a seal 112 between the inboard bearing member 68 and the valve stem 62; and a seal 114 disposed within the sealing face 76 of the head 64 to seal against the seat 78.

With reference to FIG. 2, if control air or other compressed gas is applied to the actuator port 88, the piston 86 is urged forward, and it in turn pushes the valve stem 62 forward, i.e., in the downstream direction or to the right in the drawings, so that the sealing face 76 of the head 64 is disposed snugly against the valve seat 78. If control air is applied to the actuator port 90, the piston 86 is urged in the other direction. This moves the valve stem 62 rearwardly, i.e., in the upstream direction or to the left in the drawings. This releases pressure of the sealing face 76 against the seat 78, and the seal between the face 76 of the seat 78 becomes broken. At this time, compressed gas from the reference chamber assembly 48 rushes through the bore 72 of the valve stem 62 and through the aperture 74 in the notch 70. The gas flow through the head 64 into the gas release chamber 80 places a significant pressure onto the face 76 of the head, so that the valve stem 62 is rapidly snapped into the open position shown in FIG. 4.

It should be noted that the compressed gaseous test medium can flow rapidly and without significant obstruction from the reference chamber cylinder 50, through the male member 52, the gland 46, and the bore 72 of the valve stem 62 without significant obstruction. Then, the gaseous test medium flows rapidly from within the valve stem 62 into the gas release chamber 80 and thence to the upstream end of the core. The structure including the notch 70 and the apertures 74 ensures a minimum of opposition to the flow of gas through and around the head 64 on the path to the upstream end of the core sample.

The reference chamber assembly 48 is calibrated so that the total volume of the members upstream of the valve face 78, to wit, the cylinder 50, the male member 52, the gland 46, the bore 72 of the valve stem 62, and the gas release chamber 80 about the head 64 is a predetermined standard value, such as 50 CC or 500 CC.

To perform a permeability test, a vacuum is applied to an annular port 118 of the core barrel 12 causing the sleeve 14 to expand, thus providing clearance for the core sample to be inserted into the core chamber 16. The downstream end piece 20 is placed below the core and by adjustment of the pivotal points of the side plates 34 and adjustment of the support screw 30, the core sample is pushed upward into the chamber 16 to seat against the face of the upstream end plug 38. A compressed fluid is now introduced through the annular fitting 118 into the annular space between the barrel 12 and the rubber sleeve 14 causing the sleeve 14 to expand and seal against the core sample wall, preventing any gas passage, other than flow through the sample's interior passageways. Then, control air is applied to the actuator port 88 to ensure that the valve face 76 is pressed against the seat 78. A compressed test fluid, such as compressed air, is applied to the fill port 92 at a predetermined pressure, e.g., 200 PSIG. As a result of that step, the reference cylinder contains a predetermined volume, i.e., (50 CC or 500 CC) of the test fluid at the predetermined pressure (i.e., 200 PSIG). Then the set up is ready for a permeability test run.

Figure 4:
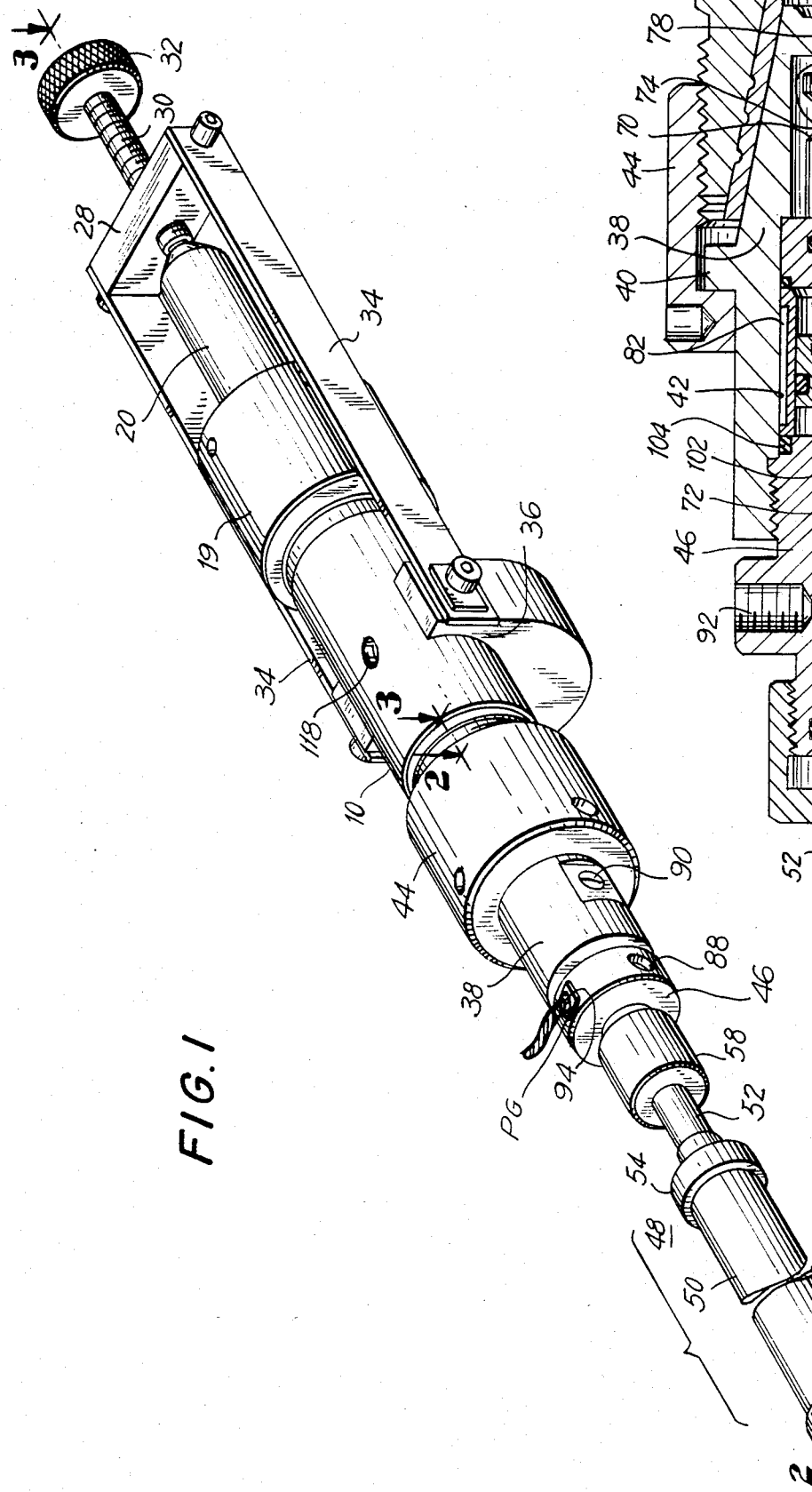
FIG. 4 is a cross sectional view showing the core holder with its valve in the open position.

Now air is applied to the actuator port 90, and the valve assembly snaps open to the position shown in FIG. 4. Substantially instantaneously, the compressed air stored in the reference chamber 48 flows through the valve seat 78 to the upstream end of the core sample. At the time that the valve assembly is opened, both the time and the pressure, as measured by the pressure gauge in the gauge port 94, are recorded as test data, for example, in the memory of a special-use or general-purpose computer. The pressure at the downstream end of the cylinder is always substantially atmospheric pressure, so that the pressure at the gauge registers the pressure differential at the gas flow through the core.

Because the reference chamber 48 has a known, fixed volume, the flow rate of gas into the sample face can be calculated from the decay over time of pressure at the upstream end of the core holder. As mentioned previously, if the gauge is a small, lightweight transducer, the natural resonance thereof can be kept to a minimum, and pressure data can be entered into a computer at close time intervals. This permits the computation of flow characteristics, for example gas permeabilities, as a function of pressure, as well as the computation of turbulence factors and Klinkenberg slip corrections by well established methods. See, for example, co-pending application Ser. No. 426,798, U.S. Pat. No. 2,867,116 (I. F. Aranofsky, et al.), and M. R. Tek, et al., "The Effect of Turbulence on Flow of Natural Gas through Porous Reservoirs", Journal of Petroleum Technology, p. 899 (1962).

This description does not include the algorithms programmed in the computer or microprocessor, as these are based on well known relationships and correlations and can be easily prepared.

For typical core samples, the time necesssary for sufficient pressure decay to calculate permeability and other flow characteristics can range between about 15 seconds and about 4 minutes.

A sleeve pressure line (not shown) is coupled to the pressure port 118. When a core sample is to be inserted into the barrel, a vacuum is supplied to the pressure line and the sleeve 19 is drawn to the wall of the barrel cavity. When the core sample has been placed into the core chamber 16 and the elements 20, 28, 30 at the downstream end of the barrel have been placed over the core sample, an appropriate sleeve pressure is placed on the line and this pressure is transmitted to the cylindrical surface of the core. The sleeve pressure approximates the overburden pressure of the core sample in its natural condition, and bears a relationship to the depth from which the core sample was taken. This pressure is generally a much higher pressure value than what is required to seal the sleeve.

In a preferred mode, two core holders are associated with a single computer in order to reduce turn-around time. In this mode, the core holders are used alternately. In such a mode, a first of the core holders is loaded and set up, while a permeability test is run on a core sample in the second holder. Then, at the end of a run, the second core holder is loaded while a permeability test is run on the sample in first core holder.

It should be appreciated that although one preferred embodiment has been described hereinabove, many modifications and variations will present themselves to those skilled in the art without departure from the scope and spirit of this invention, as defined in the appended claims.

What is claimed is:

1. Core holder apparatus for nonsteady-state measurement of flow characteristics of a geological core sample, comprising a barrel having a core chamber therein open at its ends for holding said core sample for passage of a gaseous test medium therethrough from an upstream end to a downstream end; retaining means within said barrel for retaining said core sample in said core chamber; reference pressure reservoir means for containing a predetermined volume of said gaseous test medium under a predetermined pressure, said volume to pass from said reservoir means to the upstream end of said core sample and thence therethrough and out the downstream end thereof to a lower pressure drain for said test medium; gas operated valve means coupling said reservoir means to the upstream end of said core chamber and rapidly opening for rapidly exposing the upstream end of said core sample to the gaseous test medium in said reservoir when a control gas pressure is applied to an opening actuator port of said valve means; and pressure monitoring means coupled to said reference pressure reservoir means for measuring the pressure therein decaying over time as said gaseous test medium flows therefrom through said core sample.

2. Core holder apparatus for nonsteady-state measurement of flow characteristics of a geological core sample, comprising a barrel having a core chamber therein open at its ends for holding said core sample for passage of a gaseous test medium therethrough from an upstream end to a downstream end; retaining means within said barrel for retaining said core sample in said core chamber; reference pressure reservoir means for containing a predetermined volume of said gaseous test medium under a predetermined pressure, said volume to pass from said reservoir means to the upstream end of said core sample and thence therethrough and out the downstream end thereof to a lower pressure drain for said test medium; gas operated valve means coupling said reservoir means to the upstream end of said core chamber and rapidly opening for rapidly exposing the upstream end of said core sample to the gaseous test medium, said valve means including a hollow valve stem having a head at one end thereof; a gland overfitting an end of said valve stem and permitting slidable movement therein; a valve seat disposed about the upstream end of said core chamber sealably seating against said head to close when said valve stem is urged in one direction and to unseat and open when said valve stem is urged in the opposite direction; and piston means having coupled thereto a seating actuator port and an unseating actuator port for urging said valve stem in said one direction and in said opposite direction when said control gas is applied respectively to said actuator ports; and pressure monitoring means coupled to said reference pressure reservoir means for measuring the pressure therein decaying over time as said gaseous test medium flows therefrom through said core sample.

3. Core holder apparatus for nonsteady-state measurement of flow characteristics of a geological core sample, comprising a barrel having a core chamber therein open at its ends for holding said core sample for passage of a gaseous test medium therethrough from an upstream end to a downstream end; retaining means within said barrel for retaining said core sample in said core chamber; reference pressure reservoir means for containing a predetermined volume of said gaseous test medium under a predetermined pressure, said volume to pass from said reservoir means to the upstream end of said core sample and thence therethrough and out the downstream end thereof to a lower pressure drain for said test medium; gas operated valve means coupling said reservoir means to the upstream end of said core chamber and rapidly opening for rapidly exposing the upstream end of said core sample to the gaseous test medium, said valve means including a hollow valve stem having a head at one end thereof; a gland overfitting an end of said valve stem and permitting slideable movement therein; a valve seat disposed about the upstream end of said core chamber sealably seating against said head to seat and close when said valve stem is urged in one direction and to unseat and open when said valve stem is urged in the opposite direction; piston means having coupled thereto a seating actuator port and an unseating actuator port for receiving said control gas for urging said valve stem in said one direction and in said opposite direction when said control gas is applied respectively to said actuator ports; and pressure monitoring means coupled to said reference pressure reservoir means for measuring the pressure therein decaying over time as said gaseous test medium flows therefrom through said core sample.

4. Core holder apparatus for nonsteady-state measurement of flow characteristics of a geological core sample, comprising a barrel having a core chamber therein open at its ends for holding said core sample for passage of a gaseous test medium therethrough from an upstream end to a downstream end; retaining means within said barrel for retaining said core sample in said core chamber; reference pressure reservoir means for containing a predetermined volume of said gaseous test medium under a predetermined pressure, said volume to pass from said reservoir means to the upstream end of said core sample and thence therethrough and out the downstream end thereof to a lower pressure drain for said test medium; gas operated valve means coupling said reservoir means to the upstream end of said core chamber and rapidly opening for rapidly exposing the upstream end of said core sample to the gaseous test medium, said valve means including a hollow valve stem having a head at one end thereof; a gland overfitting an end of said valve stem and permitting slidable movement therein; a valve seat disposed about the upstream end of said core chamber sealably seating against said head when said valve stem is urged in one direction and to unseat and open when said valve stem is urged in the opposite direction; means defining a generally cylindrical cavity between said gland and said valve seat having a clearance over said valve stem and head, bearing means in said cavity slidably sealing over said valve stem and dividing said cavity into a chamber over said head and an actuator cylinder over said stem, a piston on said valve stem slidably contacting the wall of said cylinder, and duct means respectively coupling said seating and unseating actuator ports to said cylinder on the upstream and downstream sides of said piston, respectively; and pressure monitoring means coupled to said reference pressure reservoir means for measuring the pressure therein decaying over time as said gaseous test medium flows therefrom through said core sample.

5. Core holder apparatus for nonsteady-state measurement of flow characteristics of a geological core sample, comprising a barrel having a core chamber therein open at its ends for holding said core sample for passage of a gaseous test medium therethrough from an upstream end to a downstream end; retaining means within said barrel for retaining said core sample in said core chamber; reference pressure reservoir means for containing a predetermined volume of said gaseous test medium under a predetermined pressure, said volume to pass from said reservoir means to the upstream end of said core sample and thence therethrough and out the downstream end thereof to a lower pressure drain for said test medium; gas operated valve means coupling said reservoir means to the upstream end of said core chamber and rapidly opening for rapidly exposing the upstream end of said core sample to the gaseous test medium, said valve means including a hollow valve stem having a longitudinal passageway therein coupled to said reservoir means and an enlarged head at one end thereof; a gland overfitting an end of said valve stem and permitting slidable movement therein; a valve seat disposed about the upstream end of said core chamber sealably seating against said head to seat and close when said valve stem is urged in one direction and to unseat and open when said valve stem is urged in the opposite direction; piston means having coupled thereto a seating actuator port for receiving said control gas for urging said valve stem in said one direction and in said opposite direction when said control gas is applied respectively to said actuator ports; said head having an angled cutout on an outer surface thereof, with a plurality of passages leading from said longitudinal passageway to said angled cutout, so that once said valve head in unseated, said gaseous test medium flows with a minimum of turbulence from said longitudinal passageway out over said head to said upstream end of said core sample; and pressure monitoring means coupled to said reference pressure reservoir means for measuring the pressure therein decaying over time as said gaseous test medium flows therefrom through said core sample.

6. Core holder apparatus according to claim 5, wherein said cutout is an angled annular cutout on a cylindrical surface of said head.

7. Core holder apparatus according to claim 5, wherein said cutout has an angled surface disposed substantially 45° towards the upstream end of said core sample.

8. Core holder apparatus for nonsteady-state measurement of flow characteristics of a geological core sample, comprising a barrel having a core chamber therein open at its ends for holding said core sample for passage of a gaseous test medium therethrough from an upstream end to a downstream end; retaining means within said barrel for retaining said core sample in said core chamber; reference pressure reservoir means for containing a predetermined volume of said gaseous test medium under a predetermined pressure, said volume to pass from said reservoir means to the upstream end of said core sample and thence therethrough and out the downstream end thereof to a lower pressure drain for said test medium; gas operated valve means coupling said reservoir means to the upstream end of said core chamber and rapidly opening for rapidly exposing the upstream end of said core sample to the gaseous test medium, said valve means including a hollow valve stem having a head at one end thereof; a gland overfitting an end of said valve stem and permitting slidable movement therein; a valve seat disposed about the upstream end of said core chamber sealably seating against said to seat and close when said valve stem is urged in one direction and to unseat and open when said valve stem is urged in the opposite direction; piston means having coupled thereto a seating actuator port and an unseating actuator port for receiving said control gas for urging said valve stem in said one direction and in said opposite direction when said control gas is applied respectively to said actuator ports, said piston means including a cylindrical sleeve surrounding said valve stem in a zone between said gland and said head defining a substantially annular space around the valve stem in said zone, a piston on said valve stem slidably contacting said sleeve, and duct means respectively coupling said seating and said unseating actuator ports to said annular space on the upstream and downstream sides of said piston, respectively; and pressure monitoring means coupled to said reference pressure reservoir means for measuring the pressure therein decaying over time as said gaseous test medium flows therefrom through said core sample.

9. Core holder apparatus for nonsteady-state measurement of flow characteristics of a geological core sample, comprising a barrel having a core chamber therein open at its ends for holding said core sample for passage of a gaseous test medium therethrough from an upstream end to a downstream end; retaining means within said barrel for retaining said core sample in said core chamber, said retaining means including a sleeve of resilient elastic material disposed between an inner surface of said barrel and said core sample, with a gas passage being provided in said barrel to said inner surface for selectively applying gas pressure against said sleeve to bias the same to said core sample to hold the latter securely in place; reference pressure reservoir means for containing a predetermined volume of said gaseous test medium under a predetermined pressure, said volume to pass from said reservoir means to the upstream end of said core sample and thence therethrough and out the downstream end thereof to a lower pressure drain for said test medium; air operated valve means coupling said reservoir means to the upstream end of said core chamber and rapidly opening for rapidly exposing the upstream end of said core sample to the gaseous test medium in said reservoir when a control gas pressure is applied to an opening actuator port of said valve means; and pressure monitoring means coupled to said reference pressure reservoir means for measuring the pressure therein decaying over time as said gaseous test medium flows therefrom through said core sample.

* * * * *